US010780114B2

(12) United States Patent
Udagawa et al.

(10) Patent No.: US 10,780,114 B2
(45) Date of Patent: Sep. 22, 2020

(54) THERAPEUTIC AGENT FOR SKIN WOUND OR ROUGH SKIN (71) Applicant: JFE MINERAL COMPANY, LTD., Tokyo (JP)

(72) Inventors: Etsurou Udagawa, Tokyo (JP); Yuko Echizenya, Tokyo (JP); Chisaki Miura, Tokyo (JP); Yoshimi Nakata, Tokyo (JP); Osamu Yamamoto, Tokyo (JP)

(73) Assignee: JFE MINERAL COMPANY, LTD., Tokyo (JP)

( * ) Notice: Subject to any disclaimer, the term of this patent is extended or adjusted under 35 U.S.C. 154(b) by 0 days.

(21) Appl. No.: 15/735,634

(22) PCT Filed: Jun. 10, 2016

(86) PCT No.: PCT/JP2016/067404
§ 371 (c)(1),
(2) Date: Dec. 12, 2017

(87) PCT Pub. No.: WO2016/199905
PCT Pub. Date: Dec. 15, 2016

(65) Prior Publication Data
US 2018/0311277 A1 Nov. 1, 2018

(30) Foreign Application Priority Data

Jun. 12, 2015 (JP) ................. 2015-119535
Mar. 4, 2016 (JP) ................. 2016-042581

(51) Int. Cl.
*A61K 33/30* (2006.01)
*A61K 8/27* (2006.01)
*A61Q 19/00* (2006.01)
*A61L 15/22* (2006.01)
*A61P 17/02* (2006.01)

(52) U.S. Cl.
CPC .............. *A61K 33/30* (2013.01); *A61K 8/27* (2013.01); *A61L 15/22* (2013.01); *A61P 17/02* (2018.01); *A61Q 19/00* (2013.01)

(58) Field of Classification Search
CPC .......... A61K 33/30; A61K 8/27; A61Q 19/00; A61L 15/22; A61P 17/02
See application file for complete search history.

(56) References Cited

U.S. PATENT DOCUMENTS

| 2003/0069045 | A1 | 4/2003 | Miyoshi |
| 2003/0133991 | A1 | 7/2003 | Monroe et al. |
| 2004/0076662 | A1 | 4/2004 | Riesinger |
| 2004/0076686 | A1 | 4/2004 | Riesinger |
| 2004/0105897 | A1 | 6/2004 | Monroe et al. |
| 2004/0170703 | A1 | 9/2004 | Hoekstra et al. |
| 2006/0029682 | A1 | 2/2006 | Monroe et al. |
| 2006/0257501 | A1 | 11/2006 | Monroe et al. |
| 2007/0009611 | A1 | 1/2007 | Monroe et al. |
| 2007/0128296 | A1 | 6/2007 | Hoekstra et al. |
| 2007/0190178 | A1 | 8/2007 | Monroe et al. |
| 2007/0298121 | A1 | 12/2007 | Monroe et al. |
| 2008/0220091 | A1 | 9/2008 | Monroe et al. |
| 2010/0196507 | A1 | 8/2010 | Monroe et al. |
| 2010/0330163 | A1 | 12/2010 | Soparkar |
| 2014/0017296 | A1 | 1/2014 | Sidenius et al. |

FOREIGN PATENT DOCUMENTS

| CN | 1337873 A | 2/2002 | |
| DE | 102006051035 | 4/2008 | |
| EP | 2233146 | 9/2010 | |
| JP | 2004-534560 | 11/2004 | |
| JP | 2005-515191 | 5/2005 | |
| JP | 2012-531421 | 12/2012 | |
| JP | 2014-511851 | 5/2014 | |
| JP | 2015-038014 | 2/2015 | |
| WO | WO 03/045366 | 6/2003 | |
| WO | 2013-012968 | 1/2013 | |
| WO | WO 2014/099165 | 6/2014 | |
| WO | WO-2014098827 A1 * | 6/2014 | ............... A61K 8/27 |
| WO | WO-2014099167 A2 * | 6/2014 | ............... A61K 8/27 |

OTHER PUBLICATIONS

D. Pirrie, et al, A New Occurrence of Diagenetic Simonkolleite from the Gannel Estuary, Cornwall, 10 Geosci. SW Eng. 018 (Year: 2000).*
J. Sithole, et al, Simonkolleite Nano-Platelets: Synthesis and Temperature Effect on Hydrogen Gas Sensing Properties, 258 Appl. Surf. Sci. 7839 (Year: 2012).*
Shobha N. Bhattachar, Laura A. Deschenes, & James A. Wesley, Solubility: It's Not Just for Physical Chemists, 11 Drug Disc. Today 1012 (Year: 2006).*
International Search Report, PCT/JP2016/067404, dated Aug. 23, 2016.
Drugs in Japan: ethical drugs 2009 edition, 2008, pp. 2 to 3, ISBN 978-4-8407-3863-7, paragraph of 'Hifu Shikkan Chiryozai 262, 264 Sanka Aen'.
Mavromichalis, I et al, Growth-promoting efficacy of pharmacological doses of tetrabasic zinc chloride in diets for nursery pigs, Can J Anim Sci, 2001, vol. 81 , No. 3, p. 387-391, ISSN 0008-3984, Abstract.
Japanese Office Action dated Apr. 18, 2017, Application No. 2017-513015.
Japanese Office Action dated Jun. 27, 2017, Application No. 2017-513015.
Korean Office Action dated Jan. 8, 2018, Application No. 10-2017-7035845.

(Continued)

*Primary Examiner* — Sean M Basquill
(74) *Attorney, Agent, or Firm* — Nixon & Vanderhye (57) ABSTRACT

Provided is a low-cost, easy-to-handle, effective therapeutic agent for wounds that is a therapeutic agent for skin wounds or rough skin that includes at least one selected from the group consisting of zinc chloride, zinc hydroxide, and zinc oxide and may include a pharmaceutically acceptable carrier.

18 Claims, 7 Drawing Sheets

(56) References Cited

OTHER PUBLICATIONS

Concise Statement of Relevance of Korean Office Action dated Jan. 8, 2018, Application No. 10-2017-7035845.
Extended European Search Report for Application No. 16807610, dated Jul. 31, 2018.
Office Action and Search Report issued in Chinese Patent Application No. 201680031330.4 dated Feb. 26, 2020, with English translation of the Search Report provided.
Non-Final Office Action issued in corresponding U.S. Appl. No. 15/735,640 dated May 1, 2020.

* cited by examiner

SINCE NO INFLAMMATORY CELL INFILTRATION WAS PRESENT WHILE GRANULATION TISSUE (FORMATION OF CAPILLARIES AND COLLAGEN FIBERS) WAS OBSERVED, THIS PERIOD WAS DETERMINED TO BE GROWTH STAGE.

THERAPEUTIC AGENT FOR SKIN WOUND OR ROUGH SKIN

TECHNICAL FIELD

The present invention relates to a therapeutic agent for skin wounds or skin roughness as well as a medical device using the therapeutic agent.

BACKGROUND ART

Zinc is the second most abundant metal in human bodies, and it has been known from a long time ago that zinc is important in healing the symptoms of dietary deficiency including dermatitis, anorexia, alopecia and impaired overall growth.

Patent Literature 1 describes in the paragraph [0013] "it was found that administration of relatively high amounts of well absorbed forms of zinc prior to or concurrently with therapeutic administration of botulinum toxin will enable responsiveness to the toxin in individuals who were previously poorly responsive, and apparently enhance the functional potency of botulinum toxin in other individuals as well." As examples of "zinc supplement," inorganic or organic zinc or combinations thereof for oral administration are described and zinc chloride ($ZnCl_2$), basic zinc chloride ($Zn_5Cl_2(OH)_8$), zinc oxide (ZnO) and zinc sulfate ($ZnSO_4$) are listed in the paragraph [0045] in Patent Literature 1.

However, use of basic zinc chloride such as simonkolleite in a therapeutic agent for skin wounds or skin roughness has not been discussed.

CITATION LIST

Patent Literatures

Patent Literature 1: JP 2012-531421 A

SUMMARY OF THE INVENTION

Technical Problems

An inexpensive, easy-to-use and effective therapeutic agent for skin wounds or skin roughness is provided.

Solution to Problems

The invention provides a therapeutic agent for skin wounds or skin roughness that has been made based on the finding that the therapeutic agent has a therapeutic effect on a skin wound or skin roughness.

Specifically, the invention provides the following:

(1) A therapeutic agent for a skin wound or skin roughness, comprising at least one selected from the group consisting of zinc chloride, zinc hydroxide and zinc oxide, and optionally a pharmaceutically acceptable carrier.

(2) The therapeutic agent for a skin wound or skin roughness according to (1), wherein the zinc chloride includes at least one selected from the group consisting of zinc chloride, zinc chloride hydroxide and zinc chloride hydroxide hydrate.

(3) A therapeutic agent for a skin wound or skin roughness, wherein, after a dissolution test by a stirring method, simonkolleite-containing zinc chloride hydroxide hydrate has an amount of dissolved $Zn^{2+}$ ions per surface area of 0.25 to 100 $\mu g/m^2$ and a pH of not less than 7.0 but less than 8.3, where the dissolution test is conducted with simonkolleite-containing zinc chloride hydroxide hydrate having a BET specific surface area of 10 to 150 $m^2/g$, a mass ratio between simonkolleite-containing zinc chloride hydroxide hydrate and saline being 1:50, and stirring being carried out at 500 rpm at 37° C. for 3 hours by means of a rotor.

(4) A therapeutic agent for a skin wound or skin roughness, wherein in a pattern of XRD diffraction peaks of simonkolleite-containing zinc chloride hydroxide hydrate, a structure $Zn_5Cl_2(OH)_8.nH_2O$ is dominant, with n being 0 to 6, where an a axis is 6.3 to 6.345, and a c axis is 23.4 to 23.7.

(5) The therapeutic agent for a skin wound or skin roughness according to any one of (2) to (4), wherein the simonkolleite-containing zinc chloride hydroxide hydrate is expressed by Formula (1):

$$Zn_{4\text{-}6}Cl_{1\text{-}3}(OH)_{7\text{-}8}.nH_2O \quad (1)$$

with n being 0 to 6, and a molar ratio between Zn and Cl is Zn/Cl=2.0 to 4.0.

(6) The therapeutic agent for a skin wound or skin roughness according to (5), wherein, when the therapeutic agent according to (5) is dissolved in saline for use with a ratio between the therapeutic agent and saline being 0.1 g/L to 100 g/L, the therapeutic agent being expressed by the Formula (1), and n=0 (anhydrous), a zinc concentration is 45 mass % to 75 mass % in terms of zinc metal with respect to the total amount of the therapeutic agent and a zinc concentration of the therapeutic agent in the saline is 0.045 g/L to 75 g/L.

(7) The therapeutic agent for a skin wound or skin roughness according to any one of (1) to (6), wherein the zinc chloride hydroxide hydrate is generated through a precipitate forming reaction between an aqueous zinc salt solution and an alkali aqueous solution.

(8) The therapeutic agent for a skin wound or skin roughness according to (7), wherein in the precipitate forming reaction, a precipitate is obtained by a reaction of $Zn^{2+}$ ions, $Cl^-$ ions and $OH^-$ ions in a reaction field where pH is controlled to not less than 6.0 but less than 7.5.

(9) The therapeutic agent for a skin wound or skin roughness according to (7) or (8), wherein the zinc chloride hydroxide hydrate contains simonkolleite expressed by the following formula:

$$M_{4\text{-}6}Cl_{1\text{-}3}(OH)_{7\text{-}8}.nH_2O$$

where M represents elemental zinc and n is 1 to 6.

(10) The therapeutic agent for a skin wound or skin roughness according to any one of (1) to (9), wherein a zinc concentration is 0.000001 g/L to 10 g/L in terms of zing metal with respect to the total amount of the therapeutic agent.

(11) The therapeutic agent for a skin wound or skin roughness according to any one of (1) to (10), wherein the skin wound or skin roughness is a skin wound or skin roughness extending from epidermis to dermis.

(12) A medical device for treating a skin wound or skin roughness, comprising: the therapeutic agent for a skin wound or skin roughness according to any one of (1) to (11) that is applied to a skin wound or skin roughness; and a wound covering material that retains the skin wound or the skin roughness in a closed environment.

(13) The medical device for treating a skin wound or skin roughness according to (12), wherein the wound covering material is at least one selected from the group consisting of a polyurethane film dressing, a hydrocolloid dressing, a polyurethane foam dressing, an alginate covering material, a hydrogel dressing, a hydropolymer, a cellulose film and a silk film.

(14) The medical device for treating a skin wound or skin roughness according to (12) or (13), wherein the therapeutic agent for a skin wound or skin roughness according to any one of (1) to (11) is applied, contained or attached on or in the wound covering material.

(15) A medical set for treating a skin wound or skin roughness, comprising the therapeutic agent for a skin wound or skin roughness according to any one of (1) to (11) and a wound covering material in combination.

(16) A production method of the therapeutic agent for a skin wound or skin roughness according to any one of (1) to (11), wherein an alkali aqueous solution is reacted with an aqueous zinc salt solution at a pH of 6.0 to 8.5, thereby obtaining a precipitate.

(17) A method of treating a skin wound or skin roughness, comprising: selecting a chemical structure of zinc chloride hydroxide referring to an amount of dissolved $Zn^{2+}$ ions per surface area as an index, for use as an effective ingredient.

(18) A method for promoting a therapeutic effect of a pharmaceutical composition, comprising: selecting a chemical structure of zinc chloride hydroxide referring to an amount of dissolved $Zn^{2+}$ ions per surface area as an index, and adding the selected zinc chloride hydroxide to the pharmaceutical composition.

(19) A method for promoting beauty effect of a cosmetic, comprising: selecting a chemical structure of zinc chloride hydroxide referring to an amount of dissolved $Zn^{2+}$ ions per surface area as an index, and adding the selected zinc chloride hydroxide to the cosmetic.

Advantageous Effects of Invention

The invention relates to a therapeutic agent effective in treating skin wounds or skin roughness.

DETAILED DESCRIPTION OF THE INVENTION

1. Therapeutic Agent of the Invention

The therapeutic agent of the invention is a therapeutic agent containing at least one selected from the group consisting of zinc chloride, zinc hydroxide and zinc oxide.

Basic zinc chloride is a chloride salt of zinc and is preferably expressed by a chemical formula $Zn_{4-6}Cl_{1-3}(OH)_{7-8} \cdot nH_2O$ ... Formula (1), where n is 1 to 6.

In the industrial field, basic zinc chloride is generally known as simonkolleite represented by the typical chemical formula $Zn_5(OH)_8Cl_2$. The substance is a dense corrosion product, whose excellent corrosion suppression effect is known, and famously promotes generation of simonkolleite to improve corrosion resistance of a plate layer.

The therapeutic agent of the invention is a therapeutic agent containing at least one selected from the group consisting of zinc chloride, zinc hydroxide and zinc oxide, where zinc chloride comprises at least one selected from the group consisting of zinc chloride, zinc chloride hydroxide and zinc chloride hydroxide hydrate.

The therapeutic agent of the invention may be formed by using or synthesizing natural or commercially available zinc chloride, zinc hydroxide and zinc oxide, or may be a mixture thereof. Zinc oxide is mentioned as a drug in the Japanese Pharmacopoeia.

For the therapeutic agent of the invention, a precipitate generated from an aqueous zinc salt solution by an alkaline precipitation process may be obtained for use. Preferably, a precipitate obtained by the reaction of $Zn^{2+}$ ions, $Cl^-$ ions and $OH^-$ ions in a reaction field where the pH is controlled to not less than 6.0 but less than 7.5 in a precipitate forming reaction to be described later, is used as the therapeutic agent of the invention. More preferably, the therapeutic agent of the invention is a therapeutic agent containing simonkolleite of zinc chloride hydroxide hydrate expressed by Formula (1) below:

$$Zn_{4-6}Cl_{1-3}(OH)_{7-8} \cdot nH_2 \quad (1)$$

where n is 0 to 6.

The therapeutic agent of the invention has preferably an amount of dissolved $Zn^{2+}$ ions of not less than 0.25 to 100 $\mu g/m^2$ and a pH of not less than 7.0 but less than 8.3, and more preferably an amount of dissolved $Zn^{2+}$ ions of 10 to 100 $\mu g/m^2$ and a pH of not less than 7.0 but less than 8.3 after a dissolution test by a stirring method, which will be described in Examples.

(Dissolution Test by Stirring Method)

The amount of dissolved $Zn^{2+}$ ions is measured in the present description, as follows: The surface areas of samples, which are produced with varying pH values at production by the same process as that for Preparation Example 2 of Examples to be described later, are measured beforehand by the BET method (BET specific surface area analyzer: High Precision, Multi-Analyte Gas Absorption Analyzer, manufactured by Quantachrome Instruments Japan G.K.). For each sample, the $Zn^{2+}$ ion concentration after stirring in saline is measured with an ICP emission spectrometer (ICPE-9000, manufactured by Shimadzu Corporation) to thereby obtain the amount of dissolved $Zn^{2+}$ ions, and then the amount of dissolved $Zn^{2+}$ ions is divided by the previously measured surface area. The mass ratio between each sample and saline is set to 1:50, and the amount of $Zn^{2+}$ ions dissolved in saline is measured after 3-hour stirring at 500 rpm at 37° C. by means of a rotor.

2. Production Method of Therapeutic Agent of the Invention

To an aqueous solution of preferably $NH_4Cl$ (ammonium chloride), serving as a chlorine source used in the alkaline precipitation process, NaOH, serving as a mineralizer, is added dropwise in such a manner that the aqueous solution is maintained at a pH of preferably not less than 6.0 but less than 7.5, and an acidic aqueous zinc salt solution containing zinc chloride or the like is added dropwise to generate a precipitate, followed by stirring for 10 to 30 hours, thereby obtaining a precipitate. The precipitate is subjected to solid-liquid separation by means of suction filtration or centrifugation, then washed with pure water or distilled water and dried in vacuum, whereby dry powder containing simonkolleite is obtained. The obtained simonkolleite-containing zinc chloride hydroxide hydrate is not limited in particle size, and when used for a therapeutic agent, the particle size thereof can be suitably adjusted by a known method. Exemplary chlorine sources include an aqueous solution of NaCl, and preferably $NH_4Cl$. The zinc source is selected from zinc sulfate, zinc chloride, zinc acetate, and zinc nitrate. For the mineralizer, an aqueous solution of $NH_3$ or NaOH may be used. The concentration ratio (molar ratio) between chlorine in the chlorine source and zinc in an aqueous zinc source solution is preferably 2:5 for reaction, and the concentration of the aqueous zinc source solution preferably falls within the range of 0.1 to 1 M. The reaction temperature is preferably 40° C. or lower, and more preferably 25° C. The obtained zinc chloride hydroxide hydrate composed primarily of simonkolleite is a mixture of a reaction product obtained through a precipitate forming reaction between an aqueous zinc salt solution and an alkali aqueous solution, a raw material which remains unreacted, a by-product, and impurities incorporated from raw materials.

Figure 1:
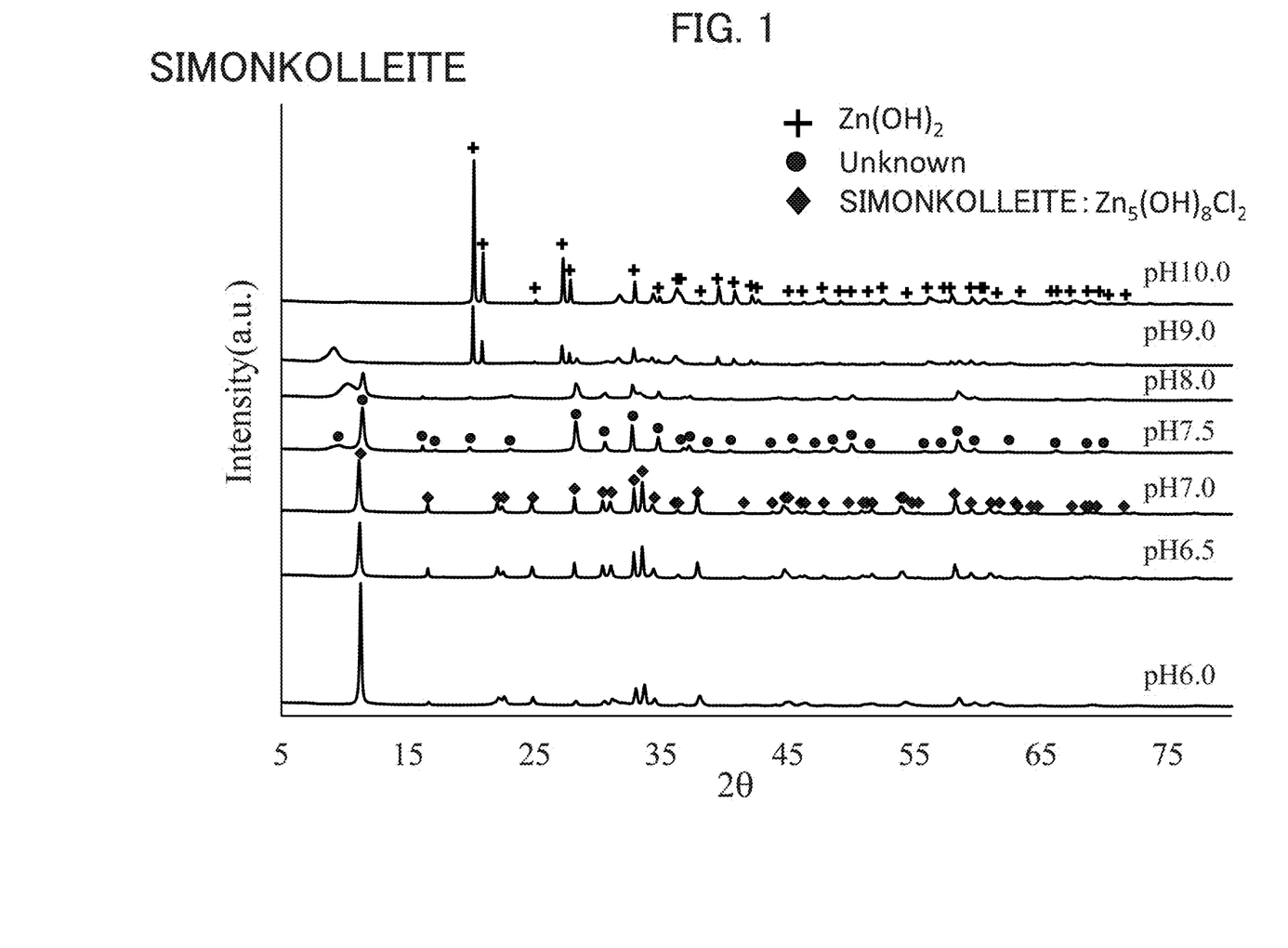
FIG. 1 is an XRD (X-ray diffraction) chart for simonkolleite obtained by a production method of Preparation Examples of the invention.

FIG. 1 shows an XRD chart of simonkolleite manufactured by a production method of Preparation Examples in the present invention under varying pH conditions. An XRD device used was D8 ADVANCE manufactured by Bruker Corporation.

As is seen in the chart of pH values of 6.0 to 7.0 at synthesis of FIG. 1, in the pattern of the XRD diffraction peaks of simonkolleite-containing zinc chloride hydroxide hydrate, the structure of $Zn_5Cl_2(OH)_8 \cdot nH_2O$ of simonkolleite is dominant, and it is preferable that the a axis be 6.3 to 6.345 and the c axis be 23.4 to 23.7. When a crystal in a pattern of XRD diffraction peaks has values falling within the foregoing ranges, the effect is high as a therapeutic agent for skin wounds or skin roughness. At pH values of 7.5 or higher, the unknown structure is dominant in a pattern of the peaks. While the production conditions for obtaining simonkolleite as the main ingredient vary depending on the types and concentrations of the chlorine source and zinc source for use, the optimal condition can be found through production with varying pH condition. The term "main ingredient" herein refers to an ingredient contained in the largest amount in a mixture, and the amount thereof is preferably not less than 60 mass %, more preferably not less than 80 mass % and even more preferably not less than 95 mass %.

To date, many studies have been done for evaluating wound healing effects by applying zinc compounds such as $ZnSO_4$, $ZnCl_2$ and ZnO to wound sites formed on experimental animals. Those compounds are substances supplying $Zn^{2+}$ ions to a wound site. Meanwhile, the fact that there is the optimum concentration of $Zn^{2+}$ ions for a wound healing effect given by $Zn^{2+}$ ions, has been reported. It is known that, while not more than 500 μmol/L of zinc ions do not exhibit toxicity to a fibroblast, a high level (not less than 15 mmol/L) of zinc ions lead to increased inflammatory cell infiltration in skin and remarkably delay reepithelization.

The pH of the body fluid composed primarily of saline is about 7.4 to about 7.5, and when, for example, basic zinc chloride composed primarily of simonkolleite of the invention is dissolved in saline, the pH is expected to vary in accordance with formation and dissolution of $Zn^{2+}$ ions. In addition, by figuring out two factors including a pH environment supplying $Zn^{2+}$ ions and/or $Cl^-$ ions and the supply of $OH^-$ ions for efficiently activating matrix metalloproteinase (MMP) enzymes that decompose matrix proteins by the aid of $OH^-$ ions of water molecules, healing further proceeds while tissue hindering healing, such as a crust, is not formed, and a scar can be prevented from remaining, so that improved QOL (quality of life) of patients can be expected.

It is known that cells actively grow and migrate in a wound healing process. When a cell migrates within a tissue or between tissues, it is necessary to locally break existing extracellular matrix. At the same time, formation of new extracellular matrix proceeds in order to remodel tissue at a wound site. In those processes, various proteolytic enzymes are involved.

The activation balance between matrix metalloproteinases (MMPs) and tissue inhibitors of metalloproteinases (TIMPs) is related to both of normal and pathologic events such as wound healing, tissue repair, vascularization, infiltration, tumorigenesis and tumor metastasis.

The MMPs are enzymes degrading extracellular collagen and are synthesized by connective tissue and cells present in connective tissue. The MMP has a zinc ion in its center, and a binding site of $Zn^+$ ion is present at an active site. Epidermal regeneration is achieved when epidermal cells migrate from a wound edge or skin appendages (e.g., hair roots, sweat glands). Thus, bonding between $Zn^+$ ions from a zinc compound and the MMPs triggers destruction of extracellular matrix, thereby promoting migration of epidermis cells.

The TIMPs are enzymes produced by fibroblasts, endothelial cells and the like, and having an inhibitory effect against the MMPs. The MMPs and the TIMPs form a 1:1 complex to inhibit collagen degradation by the MMPs. Owing to this mechanism, it is possible to suppress specific cleavage of helix sites of type I, type II and type III collagen by the MMPs, thereby promoting fibrosis at a wound site and increasing the amount of collagen in regenerated tissue.

From the above, it is conceivable that the therapeutic agent for skin wounds or skin roughness according to the invention can promote migration of cells by suitably supplying zinc ions and/or chlorine ions to a wound site, thereby increasing accumulation of collagen and promoting healing of the wound. In addition, by figuring out a pH environment supplying zinc ions and/or chlorine ions, further healing proceeds, and a tissue hindering healing such as a crust is not formed, and a scar can be prevented from remaining, so that improved QOL (quality of life) of patients can be expected.

3. The Therapeutic Agent of the Invention can be Used as an Additive for Pharmaceutical Compositions and an Additive for Cosmetics.

(1) The therapeutic agent of the invention has no drying effect and antibacterial properties compared to a zinc oxide, and is useful as an additive. The therapeutic agent of the invention is suitable for an additive used in a medical composition, which additive includes, as an effective ingredient, simonkolleite-containing zinc chloride hydroxide hydrate having an amount of dissolved $Zn^{2+}$ ions per surface area of 0.25 to 100 μg/m² and a pH of not less than 7.0 but less than 8.3 after a dissolution test by a stirring method.

(2) In addition, the therapeutic agent of the invention is suitable for an additive used in a cosmetic, which additive includes, as an effective ingredient, simonkolleite-containing zinc chloride hydroxide hydrate having an amount of dissolved $Zn^{2+}$ ions per surface area of 0.5 to 100 μg/m² and a pH of not less than 7.0 but less than 8.3 after a dissolution test by a stirring method.

In the dissolution test, the BET specific surface area of simonkolleite-containing zinc chloride hydroxide hydrate is 10 to 150 m²/g, a mass ratio between simonkolleite-containing zinc chloride hydroxide hydrate and saline is 1:50, and stirring is carried out at 500 rpm at 37° C. for 3 hours by means of a rotor.

4. Therapeutic Agent for Skin Wounds or Skin Roughness and Pharmaceutically Acceptable Carrier Thereof The invention is a therapeutic agent for skin wounds or skin roughness and may optionally include a pharmaceutically acceptable carrier. Exemplary carriers include organic solvents and inorganic solvents, more specifically, water, saline, alcohols, polyhydric alcohols, and mixtures thereof. This therapeutic agent may be processed by adding a thickener or the like so as to have a gel or paste form, thereby improving handleability.

Exemplary carriers include hydrocarbons such as α-olefin oligomer, paraffin wax, ceresin and microcrystalline wax; animal and vegetable oils such as persic oil, olive oil, beef tallow and mink oil; synthetic esters such as cetyl octanoate, isopropyl myristate and cetyl palmitate; natural animal and vegetable waxes such as jojoba oil, carnauba wax, candelilla wax, Japan wax and bees wax; sorbitan stearate; polyoxyethylene glyceryl tristearate; polyoxyethylene lauryl ether; decaglyceryl trioleate; sucrose monolaurate ester; and silicone oils and derivatives thereof such as dimethylpolysiloxane and methyl phenyl polysiloxane.

Further examples that may be used include fluororesins such as perfluoropolyether; alcohols such as ethanol, 1,3-butylene glycol, propylene glycol and diglycerine; carrageenan, xanthan gum, carboxymethyl cellulose sodium, collagen, elastin, silk, cellulose, lactoferrin and other proteins and hydrolysates thereof; and powders of anhydrous silicate, nylon powder, polyalkyl acrylate, alumina and iron oxide.

Still other examples include ultraviolet absorbers, vitamins, urea, sea-water dried products, anti-inflammatory agents, amino acids and derivatives thereof, lecithin, coloring agents, fragrances, preservatives, and oils such as egg-yolk oil, macadamia nut oil, cottonseed oil, avocado oil, coconut oil, palm oil, palm kernel oil, corn oil, peanut oil, beef tallow and carnauba wax.

Still other examples include bees wax, liquid paraffin, lanolin, squalane, stearic acid, laurates, myristates, isostearyl alcohol, purified water, electrolyzed water and ethyl alcohol. That is, any substance blended in both of cosmetics and quasi drugs in general is usable as a carrier of the therapeutic agent for skin wounds or skin roughness according to the invention. A carrier is not necessarily used.

For instance, other optional ingredients that may be added to the therapeutic agent for skin wounds or skin roughness according to the invention are selected depending on the substance actually added to a cosmetic or a quasi drug. Although not strictly distinguishable, exemplary humectants include glycerol, sorbitol, polyethylene glycol, pyrrolidone carboxylic acid and its salt, collagen, 1,3-butylene glycol, hyaluronic acid and its salt, chondroitin sulfate and its salt, and xanthan gum.

Exemplary antioxidants include ascorbic acid, α-tocopherol, dibutylhydroxytoluene and p-hydroxyanisole. Exemplary surfactants include sodium stearyl sulfate, diethanolamine cetyl sulfate, polyethylene glycol monostearate, ethylene glycol monostearate, polyoxyethylene hydrogenated castor oil, soybean lysophospholipid liquid, and polyoxyethylene sorbitan monooleate.

Exemplary preservatives include phenoxyethanol, ethylparaben, butylparaben, and inorganic pigments such as zinc oxide.

Exemplary antiphlogistic agents include glycyrrhizic acid derivatives, salicylic acid derivatives, hinokitiol, zinc oxide and allantoin.

Exemplary whitening agents include placental extract, glutathione, *saxifraga sarmentosa* extract, ascorbic acid derivatives and arbutin.

Exemplary blood circulation promoting agents include γ-oryzanol and dextran sulfate sodium.

Exemplary antiseborrheic agents include sulfur and thianthol.

Exemplary thickeners include carboxyvinyl polymer.

Exemplary pH adjusters include lactic acid, citric acid, malic acid, glycolic acid, sodium hydroxide and hydrotalcite.

The concentration of the therapeutic agent is not particularly limited, but when the therapeutic agent is dissolved in saline for use with the ratio between the therapeutic agent and saline being 0.1 g/L to 100 g/L, the therapeutic agent being the one expressed by Formula (1) above, and n=0 (anhydrous), the therapeutic agent for skin wounds or skin roughness having a zinc concentration of 45 mass % to 75 mass % in terms of zinc metal with respect to the total amount of the therapeutic agent and a zinc concentration of the therapeutic agent in the saline of 0.045 g/L to 75 g/L is preferred. The concentration within the foregoing ranges leads to a high therapeutic effect.

5. Medical Device for Treating Skin Wounds or Skin Roughness and Wound Covering Materials The therapeutic agent of the invention is effective at treating skin wounds or skin roughness extending from the epidermis to the dermis without limitation. The therapeutic agent of the invention is effective in treating skin wounds or skin roughness of full-thickness skin deficiency extending from the epidermis to the dermis.

When the therapeutic agent of the invention is applied to a skin wound or skin roughness and a wound covering material is further used in combination, a medical device for treating skin wounds or skin roughness that retains the skin wound or the skin roughness in a closed environment is achieved. The expression "applied to a skin wound or skin roughness" may refer to direct application to a skin wound or skin roughness or application to skin in an area around a skin wound or skin roughness. A wound covering material is a medical device that retains a skin wound or skin roughness in a closed environment. A medical device in another embodiment may be configured such that the therapeutic agent of the invention is applied, contained or attached on or in a wound covering material and the wound covering material on or in which the therapeutic agent of the invention is applied, contained or attached retains a skin wound or skin roughness in a closed environment.

Wound Covering Material

In healing of skin wounds or skin roughness, there are two cases of healing in a dry environment and healing in a wet environment. In healing in a dry environment, although no wound covering material is applied in some cases, generally a breathable wound covering material is applied to protect a wound surface or a rough skin part. There are wound covering materials of gauze type, bandage type and breathable film type.

The therapeutic agent for skin wounds or skin roughness according to the invention can provide a closed environment using a wound covering material to retain a wound in a further proper wet environment, and is therefore effective at treatment. When the therapeutic agent of the invention that is an inorganic material and a wound covering material that is an organic material are combined, the organic and inorganic materials are hybridized, leading to a great synergy.

In use of the therapeutic agent of the invention, a liquid form may be employed with the use of saline or the like as the solvent and, when a wound has exudate and is wet, a powder dosage form may be employed. Viscous forms and gels between the above forms may be employed, if necessary. The therapeutic agent for skin wounds or skin roughness according to the invention can provide a closed environment using a wound covering material and, in addition, be made to take a liquid or powder dosage form so as to maintain a wet state suitable for each wound, and is therefore effective at treatment in a wet environment. In either of liquid and powder dosage forms, when the therapeutic agent of the invention is used along with a wound covering material, tissue hindering healing such as a crust is not formed, and a scar can be prevented from remaining, so that improved QOL (quality of life) of patients can be expected.

Healing of wounds can be promoted by providing a closed environment using the following wound covering materials:

1) Polyurethane Film Dressing

Examples include, by the trade names, Tegaderm (manufactured by 3M), Opsite Wound (manufactured by Smith & Nephew plc), I V3000 (manufactured by Smith & Nephew plc) and Bioclusive (manufactured by Johnson & Johnson). They are polyurethane film dressings formed of transparent films each having one side constituting an adhesive surface and each of which allows steam and oxygen to permeate therethrough so that the inside is not filled with steam. They are used for the purposes of protection of non-bleeding wound surfaces, shallow pressure ulcers (only redness) or blisters, and prevention of pressure ulcers, and are useful in sealing alginate covering materials and hydrogels, which will be described later.

2) Hydrocolloid Dressing

Examples include, by the trade names, Duoactive (manufactured by ConvaTec Inc.), Comfeel (manufactured by Coloplast Corp.), Tegasorb (manufactured by 3M) and Absocure (manufactured by Nitoms, Inc.). They are of sheet type with the outer side constituting a waterproof layer and the inner side constituting an adhesive surface containing hydrophilic colloid particles. Their sizes and shapes vary. For the thickness, some dressings are formed using polyurethane foam to provide cushioning properties and are thus thick (Duoactive, CGF), while some are very thin and flexible (manufactured by Duoactive ET). While those of sheet type are used generally, those of paste type (manufactured by Comfeel Paste) and those of granular type (Duoactive) are used for pressure ulcers with a recess or a sinus. Owing to the outer waterproof layer that blocks the affected part from the air, it is possible to, especially in the case of a pressure ulcer in the sacral region, protect a wound surface from urine and fecal incontinence. The hydrophilic colloid particles on the inner side absorbs exudate and thereby become wet gel, thus providing a wet environment. Note that oxygen in the air is blocked. Since colloid particles on a wound surface gelate, the dressing does not adhere to the wound surface. For fresh wounds, there is Duoactive that is thin.

3) Polyurethane Foam Dressing

Examples include, by the trade name, Hydrosite (manufactured by Smith & Nephew plc). The outermost side is formed from a polyurethane film impervious to water, the innermost side is formed of non-adherent thin polyurethane, and a thick layer of hydrophilic absorbent foam is sandwiched therebetween. The middle layer has high water absorbing properties, absorbs exudate and holds a moderate amount of moisture, thereby maintaining a wet environment of a wound surface. Therefore, they are used for a heavily exuding wound surface. If used for a heavily exuding pressure ulcer, hydrocolloid quickly dissolves, and surrounding skin may excessively macerate. In such a case, polyurethane is more convenient. In addition, since the dressing itself does not dissolve and does not remain on the wound surface, the handling is extremely easy.

They are usable for all types of skin loss wounds if they are fresh wounds, and the application to fingertip wounds is preferable. A fingertip area is a portion easily hit even in normal times, and a hit against a wound site in a fingertip wound is accompanied with severe pain.

When a fingertip area is covered by Hydrosite, however, since the dressing itself is thick and has cushioning properties, the impact of hitting is reduced, which is advantageous. Basically, the dressings themselves are non-adherent and need to be fixed with an adhesive bandage or the like. However, when the patient is an elderly person having extremely fragile skin and the skin is likely to be torn as if "wet Shoji paper is torn," only a bandage may be wrapped without fixation with an adhesive bandage.

4) Alginate Covering Material

Examples include, by the trade names, Kaltostat (manufactured by ConvaTec Inc.), Sorbsan (manufactured by Alcare Co., Ltd.), Algoderm (manufactured by Medicon, Inc.) and Kurabio (manufactured by Kuraray Co., Ltd.). They are formed of nonwoven fabric obtained by processing alginate (calcium salt for Sorbsan and Algoderm; a mixture of calcium salt and sodium salt for Kaltostat) extracted from kelp, which is a seaweed, into a fibrous form. Alginate absorbs 15 to 20 times as much moisture as its own weight, and gelates upon absorption of moisture containing sodium ions such as exudate. This gel maintains a wet environment of a wound surface. In addition, they have an extremely strong hemostatic effect. This is exerted upon emission of calcium ions at gelating. They are usually sealed with a film dressing for use. Among several types of products, Kaltostat has a low gelation rate and is hardly broken owing to its thick and hard fibers, whereas Sorbsan has thin fibers and therefore becomes soft gel and is easily broken; however, there is no great difference therebetween in actual use. Bleeding that may occur when a wound surface is brushed in the case of, for instance, a contusion, can be treated with an alginate covering material. Because of the foregoing characteristics, this type of covering materials are preferably used for "skin loss wounds accompanied by bleeding."

5) Hydrogel Dressing

Examples include, by the trade names, Gelibalm (manufactured by Taketora Holdings Co., Ltd.), Nu-Gel (manufactured by Johnson & Johnson), Intrasite (manufactured by Smith & Nephew plc), GranuGEL (manufactured by ConvaTec Inc.) and Clearsite (manufactured by Nippon Sigmax Co., Ltd.). They look like "transparent ointment" at first glance, but hydrophilic polymer molecules form cross-links, take on the matrix structure and contain moisture therein.

The type of polymer varies, some of the dressings include a thickener, and the amount of moisture varies for each product. The amount of contained moisture widely varies from 97% to about 60%. They are usually sealed with a film dressing for use. They are effective for "relatively dried open wound," i.e., a less exuding wound surface. They are also usable in an open wound that is a deep recess. When a pressure ulcer in a black stage as covered by a black crust is sealed with this covering material, autolysis is accelerated, thus facilitating debridement. When skin around a wound is fragile, sealing with a film dressing is difficult; in this case, gel is directly covered by gauze, which is effective enough.

6) Hydropolymer

Examples include, by the trade name, Tielle (manufactured by Johnson & Johnson). A hydropolymer absorption pad to be brought into contact with a wound has the characteristics that it absorbs exudate and swells toward exudate (the volume thereof increases). The main ingredient is hydrophilic polyurethane foam containing a small amount of acrylic polymer. When exudate is present, it swells toward the exudate. More specifically, when used for a recessed wound, this covering material protrudes in such a manner as to conform to the recess shape and softly fits into the wound surface. It is applicable to skin soft tissue loss wounds that are produced with post-operative wound dehiscence, flap necrosis or the like and extend broadly and deeply.

7) Silk Film

Silk fibroin, which has been used in the form of raw silk, has excellent strength, biocompatibility and biodegradablility, and silk can be used as a scaffold ingredient for encouraging regeneration of, for instance, teeth, bones, cartilages, eye tissue and blood vessels.

When a silk film, nonwoven fabric or the like is used as the wound covering material in combination with the therapeutic agent for skin wounds or skin roughness according to the invention, this should be effective at migration and growth of fibroblasts. A polyurethane film may be put on a surface of a silk film in order to establish a wet environment in a closed environment.

EXAMPLES

The present invention is specifically described below with reference to Examples, which by no means limit the scope of the present invention.

Preparation Example 1

In a reaction vessel, 500 mL of 0.08 M aqueous ammonium chloride solution was prepared, and separately, 1,000 mL of 0.1M aqueous zinc chloride solution was prepared as a dropping reaction solution. As a pH adjusting liquid, 30 mass % aqueous sodium hydroxide solution was prepared.

The aqueous zinc chloride solution and the aqueous sodium hydroxide solution were added dropwise under stirring with the pH of the aqueous ammonium chloride solution being maintained at 6.5 by means of a pH controller connected to a pump. After all of the aqueous zinc chloride solution was added dropwise, the reaction solution was stirred for 16 hours for conditioning.

Thereafter, the reaction solution was separated into solid and liquid fractions by centrifugation, and washing with water and centrifugation of the resulting solid were repeated three times. The precipitate thus washed was dried in vacuum, thereby obtaining simonkolleite having the composition range presented by Formula (1).

Preparation Example 2

Respective samples including Production Example 1 (pH: 6.5) were produced through the same process as that for Preparation Example 1 with varying pH values at synthesis from 5.5 to 10. At a pH of 5.5, the precipitate was not obtained because of too low a pH value.

(Dissolution Test)

Figure 7:
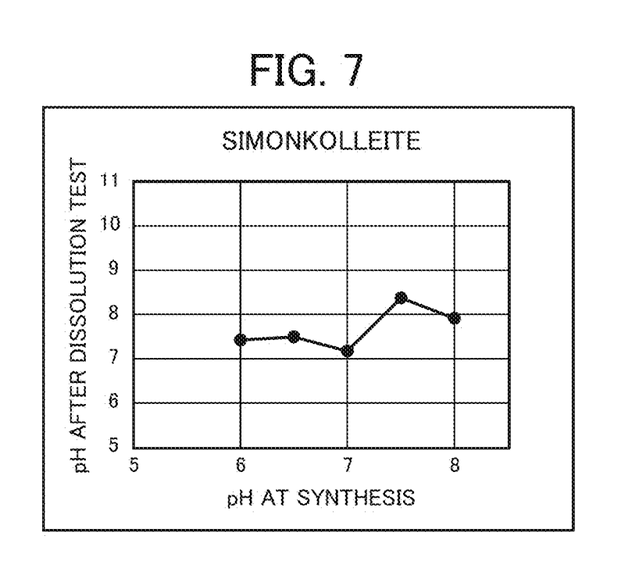
FIG. 7 is a graph showing the relationship between the pH of simonkolleite at synthesis and that after a dissolution test.

A dissolution test by a stirring method was conducted on 0.6 g each of dry powders obtained in Preparation Example 2 using 30 g of saline, and the amount of dissolved $Zn^{2+}$ ions and the pH were measured. The dissolution test was conducted with simonkolleite-containing zinc chloride hydroxide hydrate adjusted to have a BET specific surface area of 10 to 150 $m^2/g$, the mass ratio between simonkolleite-containing zinc chloride hydroxide hydrate and saline being 1:50, and stirring being carried out at 500 rpm for 3 hours by means of a rotor. Then the pH and the amount of dissolved $Zn^{2+}$ ions after the dissolution test were measured. The results thereof are shown in FIGS. 7 and 8 and Table 1.

Figure 8:
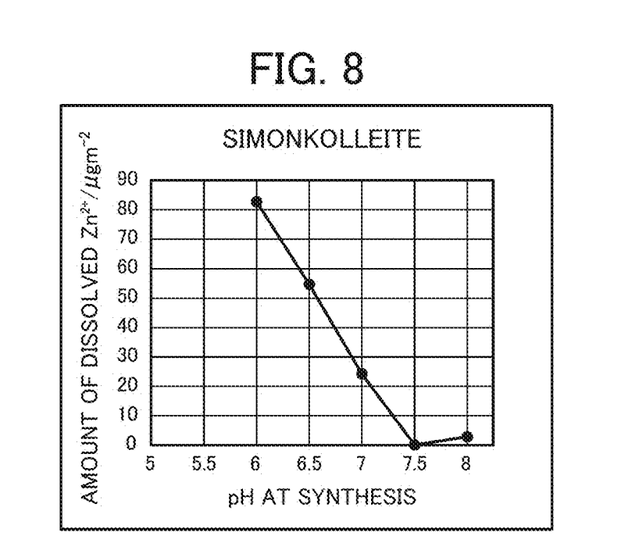
FIG. 8 is a graph showing the relationship between the pH of simonkolleite at synthesis and the amount of dissolved $Zn^{2+}$ ions after the dissolution test.

As shown in FIG. 8, the vicinity of pH 7.5 is deemed to be a singular point in synthesis of simonkolleite-containing zinc chloride hydroxide hydrate, and improvements in the yield and crystallinity of simonkolleite are seen at a pH of less than 7.5. On the other hand, it is assumed that at a pH of 7.5 or higher, a different phase is present, while at a pH of 8.5 or higher, zinc hydroxide is dominantly synthesized.

TABLE 1

| pH at synthesis | 5.5 | 6 | 6.5 | 7 | 7.5 | 8 |
|---|---|---|---|---|---|---|
| pH after dissolution test | — | 7.42 | 7.49 | 7.17 | 8.37 | 7.91 |
| Amount of dissolved $Zn^{2+}$ ions after dissolution test ($\mu g/m^2$) | — | 82.7 | 54.6 | 24.2 | 0.08 | 2.91 |

Example 1

To an SD rat weighing about 500 g, 2% Sedeluck (xylazine) was administered at 0.2 mL/500 g by intramuscular injection for sedation, and general anesthesia was given by means of 2% Sevoflurane inhalation anesthetic. After local anesthesia was given by administering xylocaine (lidocain+ 2% adrenaline) to a ventral part of the rat, a full-thickness skin loss wound having a diameter of 10 mm and extending from the epidermis to the subcutaneous tissue was formed, 0.01 g of powder of Preparation Example 1 above was applied to the formed full-thickness skin loss wound, and then the wound was covered by Duoactive being a medical wound covering material.

(Tissue Staining, Haematoxylin and Eosin (H-E) Staining)

The method of tissue staining involves, in this order, trimming (excising) a wound site; fixing in formalin; degreasing treatment (24-hour immersion in xylene); and dehydration treatment.

The dehydration treatment involves immersing in 70% ethanol for 12 hours to remove ethanol through volatilization, dehydrating in 80% ethanol, 90% ethanol and 95.5% ethanol for 30 minutes each, and washing with xylene two times.

The above was followed by, in this order, embedding treatment of a specimen in paraffin; forming a section; and H-E staining.

Figure 5:
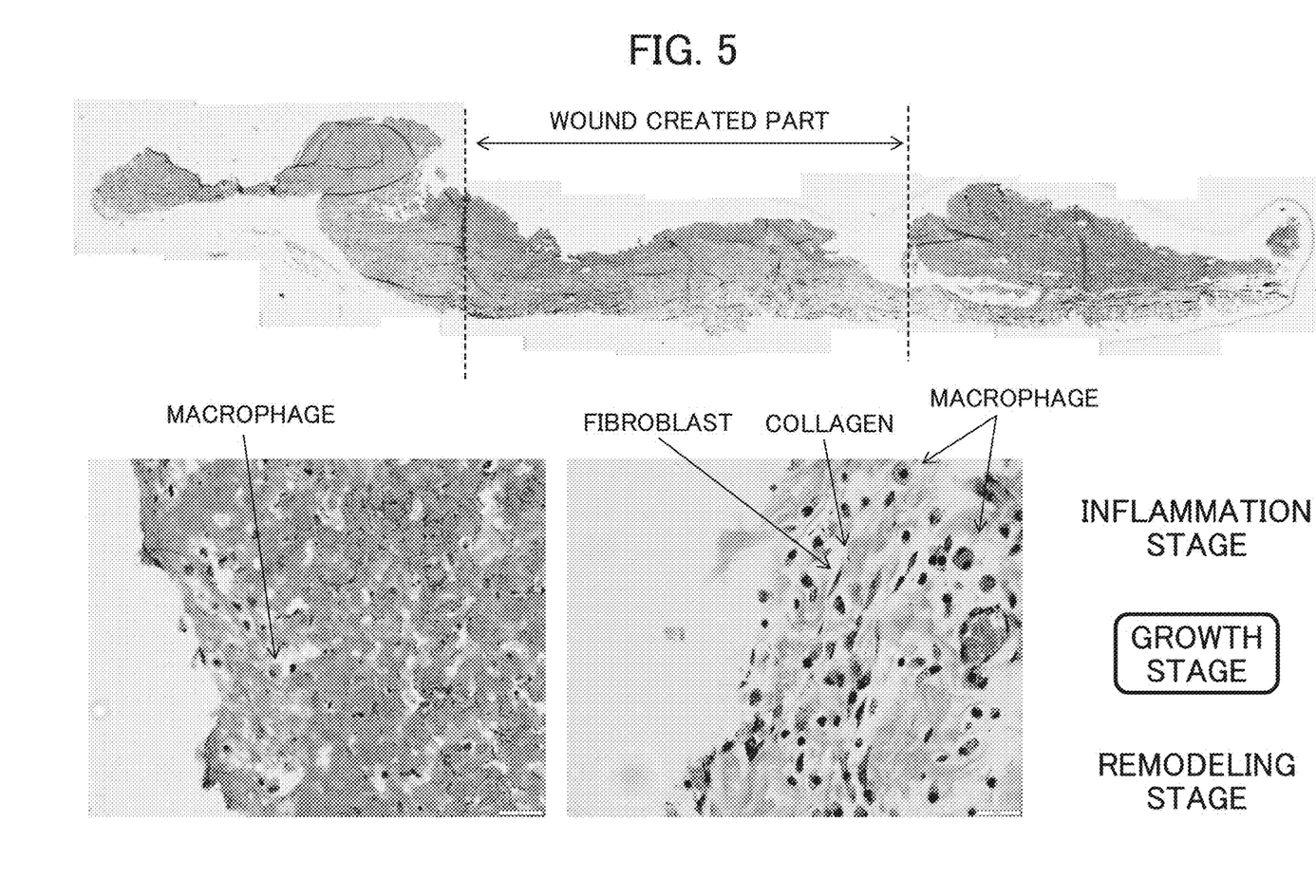
FIG. 5 shows micrographs illustrating histological evaluations of a wound created part after one week in Example 1.
Figure 6:
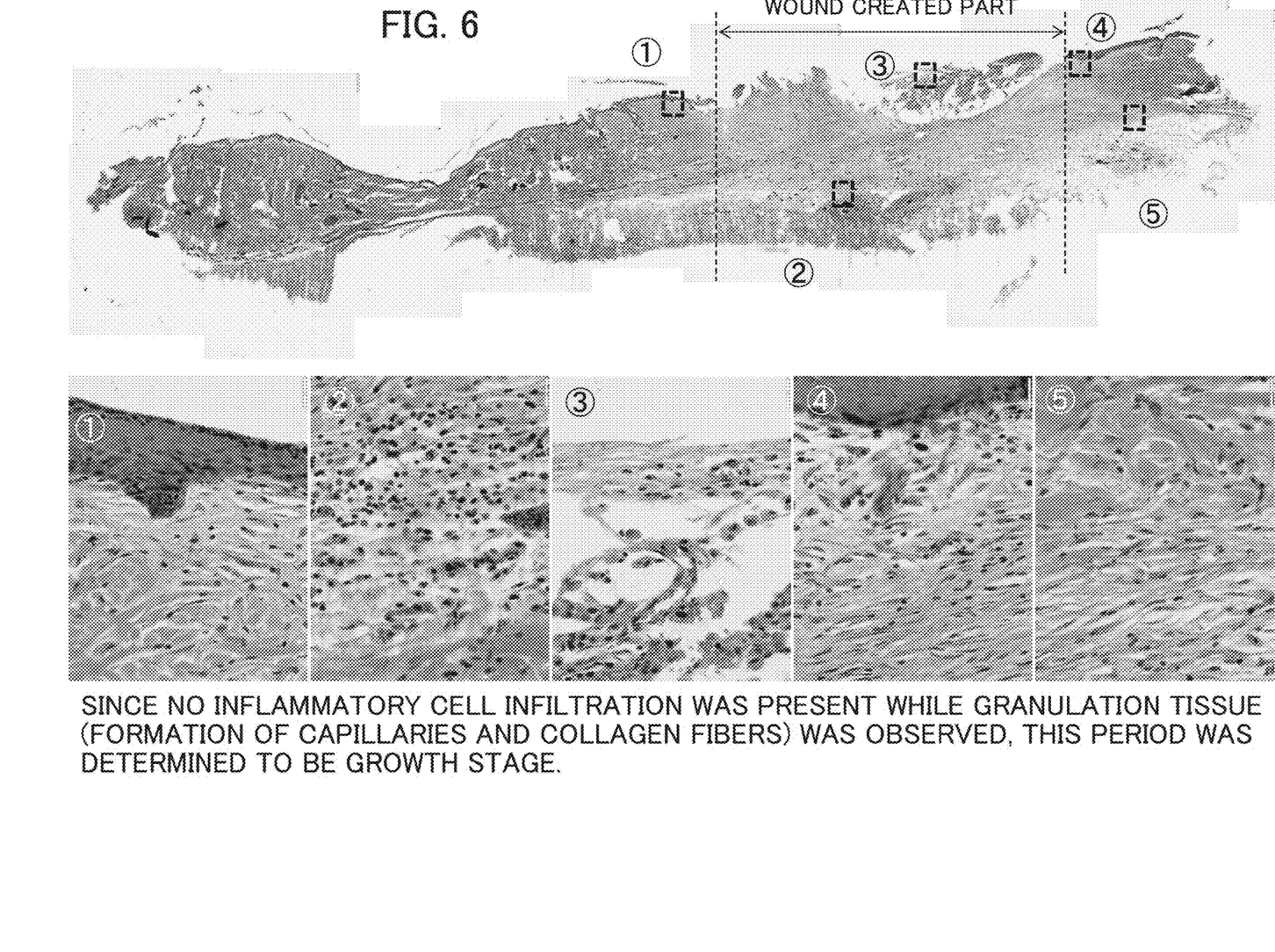
FIG. 6 shows micrographs illustrating histological evaluations of a wound created part 2 and a wound created part 3 after two weeks in Example 1. In addition to the wound created parts, parts 1, 4 and 5 are also shown.

Cell nuclei were stained in blue-violet color with haematoxylin, and the cytoplasm, collagen fibers and muscle fibers were stained in red color with eosin. Thereafter, the stained specimen is set to obtain a preparation and observed with a microscope. The observation result is shown in FIGS. 5 and 6.

The observation result of the healed site after one week of coverage by a wound covering material (FIG. 2): In the sample that was applied with the therapeutic agent of the invention obtained in Preparation Example 1 and was covered by a wound covering material one week ago, white tissue is observed at the wound site, whereas in the control to which the therapeutic agent of the invention was not applied but only covered by Duoactive being a medical wound covering material, the peritoneum is clearly recognized and the wound is not healed.

The observation result of the healed site after two weeks of coverage by a wound covering material (FIG. 3): In the sample that was applied with the therapeutic agent of the invention obtained in Preparation Example 1 and was covered by a wound covering material two weeks ago, a size reduction of the wound site is explicitly observed, and the peritoneum is not recognized. On the other hand, in the control to which the therapeutic agent of the invention was not applied, a slight size reduction of the wound site is recognized but an unhealed site at which the peritoneum is recognized is also observed.

(Measurement Method of Reepithelization Rate)

Figure 2:
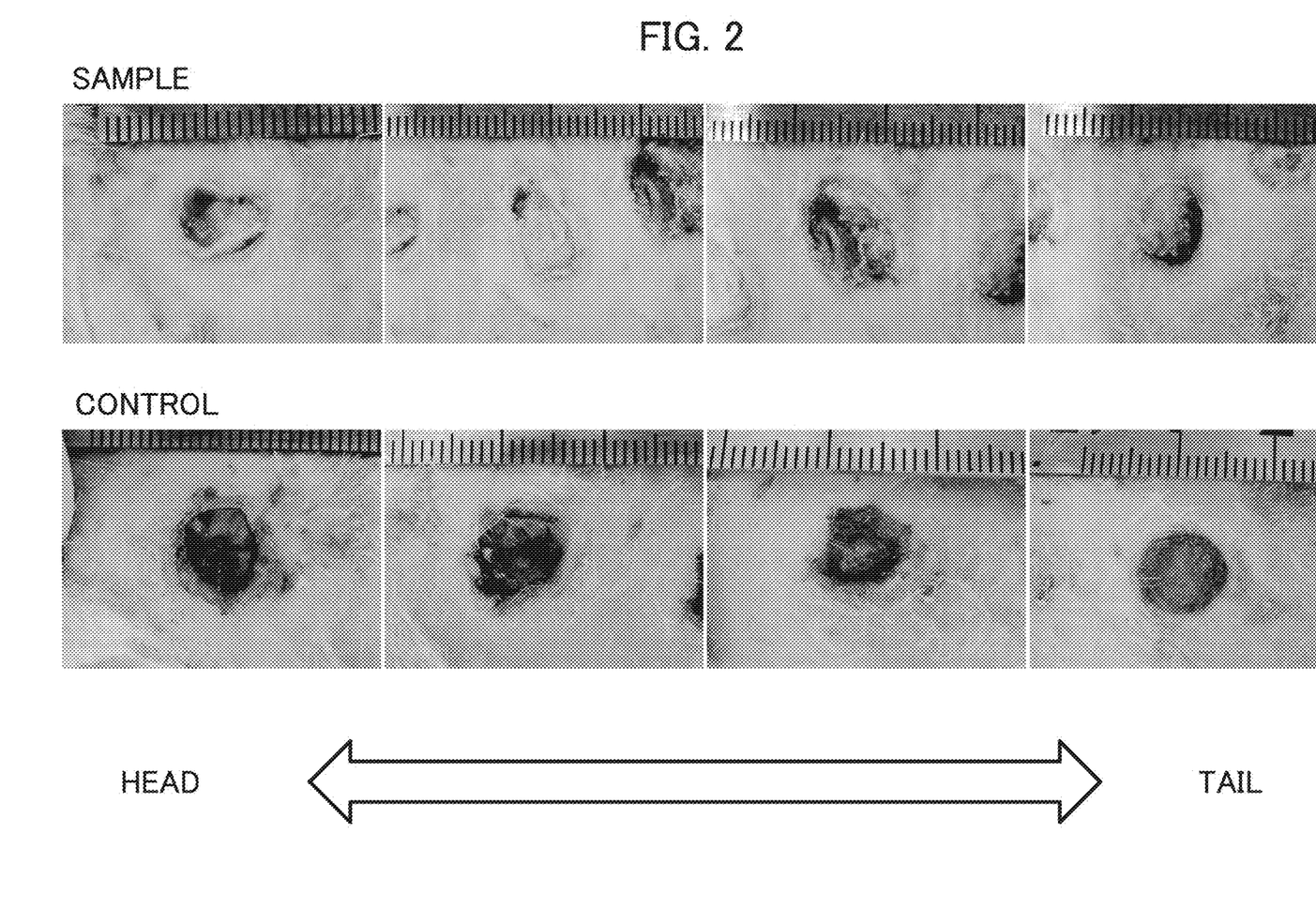
FIG. 2 shows photographs of observation results of healed sites in wound parts and a control after one week in Example 1.
Figure 3:
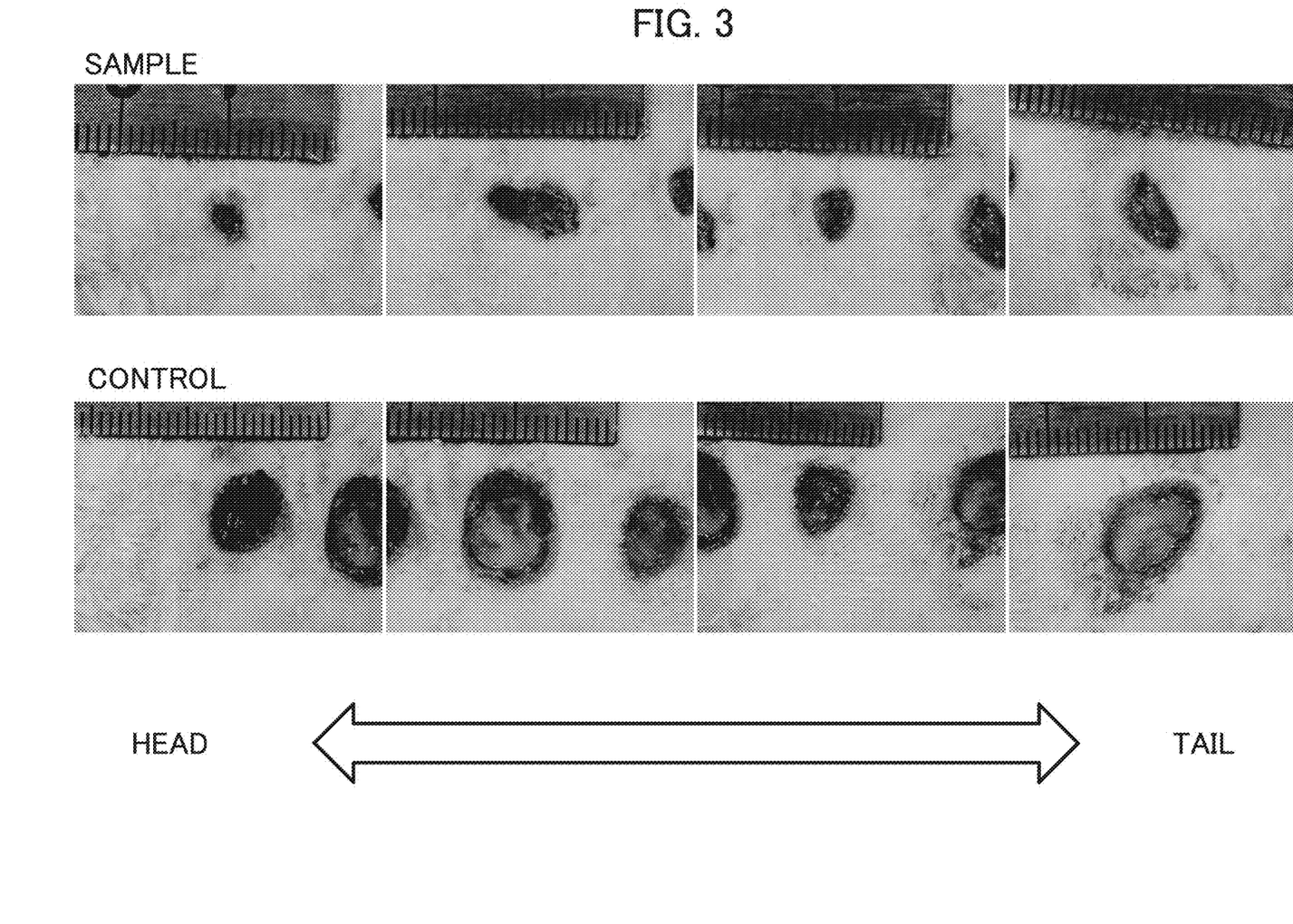
FIG. 3 shows photographs of observation results of healed sites and a control after two weeks in Example 1.

Skin is photographed with magnification at the time of wound production and after treatment, the early wound site at the time of wound production is measured and drawn by a solid line on the photographs of the site each photographed after one week and after two weeks, the area of the early wound site $W_0$ is measured, the area of an unhealed site (Wt) after treatment is measured using Image J [an open source released on the website; Wayne Rasband (NIH)], and the reepithelization rate is calculated from the measured areas using the formula below to obtain a percent value. The reepithelization rates after treatment as shown in FIGS. 2 and 3, together with those of the control, are illustrated in Table 2 and FIG. 4.

Reepithelization Rate (%)=$(W_0-Wt)/W_0 \times 100\%$

TABLE 2

| Duration (weeks) | Progress observation | |
| --- | --- | --- |
| | Comparative Example | Example of the invention |
| 1 | 23.08 | 22.04 |
| 2 | 39.88 | 76.38 |

Figure 4:
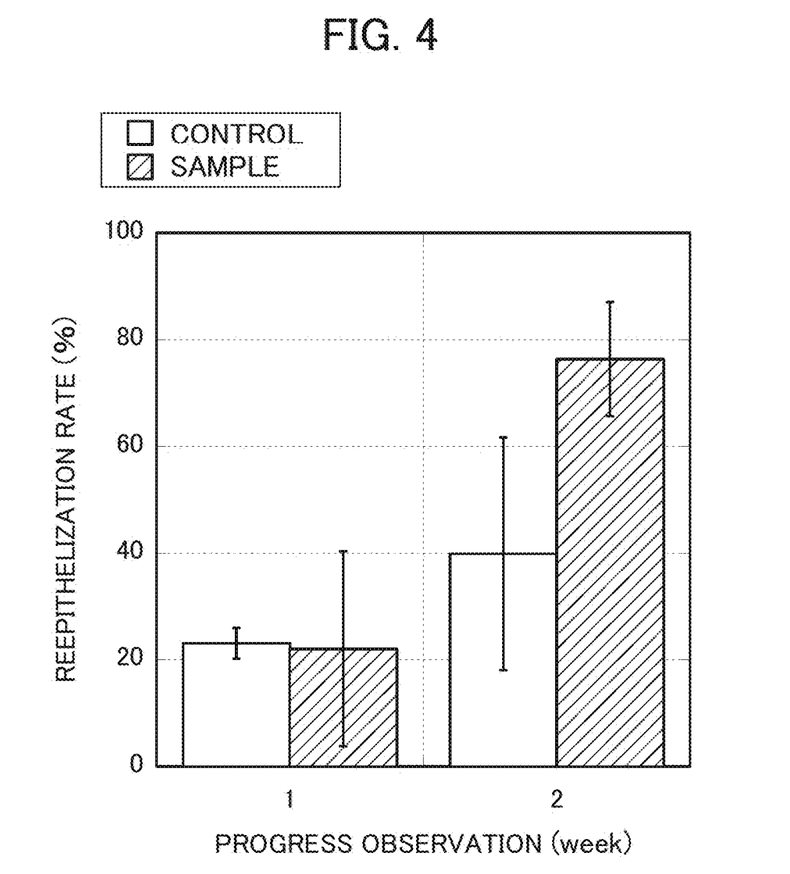
FIG. 4 is a graph illustrating the results shown in Table 2.

As seen from the result shown in Table 2 and FIG. 4, the reepithelization rate of the Example of the invention (sample) after two weeks was about 1.9 times as high as that of the Comparative Example (control).

Reepithelization rate: The t-test was performed on two data groups of the Comparative Example and the Example of the invention after two weeks having different dispersions of reepithelization rates. Although three wounds were chosen from four wounds and subjected to the test, no significant difference was seen with relatively large error bars, when the four wounds were used in calculation, a significant difference of the Example of the present invention was recognized. In calculation of the reepithelization rate, tissue in white color in the control was evaluated as an unhealed region.

Calculation using the four wounds is shown in Table 3.

TABLE 3

| | Comparative Example | Example of the invention |
| --- | --- | --- |
| Number of samples | 4 | 4 |
| Average | 28.62 | 74.47 |
| Dispersion | 823.21 | 91.02 |
| Standard deviation | 28.69 | 9.54 |
| Standard error | 14.35 | 4.77 |
| Average difference | −45.84 | |

TABLE 3-continued

| | Comparative Example | Example of the invention |
| --- | --- | --- |
| Degree of freedom | 3 | |
| t-value | −3.03 | |
| p value at t-test | 0.0435 | |

FIGS. 5 and 6 are micrographs of cross sections of skin for showing histological observation results each after a lapse of one week and after a lapse of two weeks. Upper parts of FIGS. 5 and 6 show figures of entire skin with a magnification of 36, while lower parts of FIGS. 5 and 6 show enlarged figures, with a magnification of 360, of sites indicated in the upper part figures.

In FIG. 5, the upper figure illustrates the healing condition of the wound created part in the Example of the present invention after one week, and enlarged figures are shown below. In FIG. 6, the upper figure illustrates wound created sites 2 and 3, while the lower figures are micrographs showing histological evaluations of the wound created sites 2 and 3 in the wound created part shown in the upper figure after two weeks. Micrographs each showing histological evaluations of a site 1, a site 4 and a site 5 in addition to the wound created sites are also shown, and the progress in healing of the wound is compared with the state of normal skin.

[Observation of tissue after one week (FIG. 5)]: When the therapeutic agent of the invention was applied, collagen, fibroblast and macrophage were observed; this period is deemed to be the growth stage. Since white tissue is considered as granulation tissue, regarding white tissue as healed tissue in calculation of the reepithelization rate, the therapeutic agent of the invention can be determined to have extremely high capability of skin regeneration.

[Observation of tissue after two weeks (FIG. 6)]: Infiltration of inflammatory cells was not found while granulation tissue (formation of capillaries and collagen fibers) was observed; this period can be determined to be the growth stage.

The observation results have revealed that the therapeutic agent of the invention including simonkolleite is an effective wound treatment material. The therapeutic agent can regenerate skin or a hair root without inflammation. Therefore, the therapeutic agent of the invention has a therapeutic effect on a skin wound or skin roughness extending from the epidermis but not reaching the dermis, a therapeutic effect on a skin wound or skin roughness extending from the epidermis to the dermis, or a therapeutic effect on a skin wound or skin roughness extending from the epidermis to the dermis, i.e., a full-thickness skin loss. The foregoing results reveal that the therapeutic agent of the invention has a healing effect on not only skin wounds mentioned in Examples but also similar wounds resulting from severe skin roughness.

Example 2

Full-thickness skin loss wounds were formed in the same manner as in Example 1, applied separately with the respective powders of Preparation Example 2, and then covered by Duoactive being a medical wound covering material. The therapeutic agents of the invention that were obtained under the production condition at a pH within the range from not less than 6.0 but less than 7.5 and that led to a reepithelization rate between 80% and 90% have excellent healing effects.

Table 4 below shows pH values after the dissolution test and the results of evaluation on wound healing effects (reepithelization rate, collagen regeneration, hair bulb regeneration, granulation tissue formation) after two weeks.

TABLE 4

| | | | | | | | |
|---|---|---|---|---|---|---|---|
| pH at syntehsis | 5.5 | 6 | 6.5 | 7 | 7.5 | 8 | — |
| pH after dissolution test | — | 7.42 | 7.49 | 7.17 | 8.37 | 7.91 | — |
| Amount of dissolved $Zn^{2+}$ ions after dissolution test ($\mu g/m^2$) | — | 82.7 | 54.6 | 24.2 | 0.08 | 2.91 | — |
| Healing condition after two weeks | | | | | | | Control |
| Degree of reepithelization | — | 1.9 | 1.9 | 1.8 | 1.4 | 1.3 | 1 |
| Collagen thickness | — | Excellent | Excellent | Excellent | Good | Good | Fair |
| Collagen orientation | | Excellent | Excellent | Excellent | Fair | Fair | Poor |
| Hair bulb | — | Excellent | Excellent | Excellent | Good | Almost good | Poor |
| Granulation tissue formation | | Excellent | Excellent | Good | Almost good | Almost good | Good |

A method of evaluation shown in Table 4 is as follows: The reepithelization rate was evaluated by the foregoing measurement method with taking the control as 1; For collagen, the state where thick collagen fibers extend in one direction was observed; For a hair bulb, observation results are given on whether a hair bulb is recognizable; For granulation tissue formation, evaluations are given on whether tissue composed of capillaries and fibroblasts is observable.

Collagen: For collagen, the thickness and orientation of collagen fibers were evaluated as compared to a healthy skin cell.

Collagen: For collagen, the thickness and orientation of collagen fibers were treated as indexes as compared to a healthy skin cell.

Collagen thickness: Poor; Considerably thin
  Fair; Thin
  Good; Slightly inferior
  Excellent; Almost same degree
Collagen orientation: Poor; Disordered
  Fair; Considerably inferior
  Good; Slightly inferior
  Excellent; Almost same degree
Hair bulb: Poor; No hair bulb is formed.
  Almost good; Hair bulb formation is weak.
  Good; Hair bulbs are formed.
  Excellent; Hair bulb formation is notably recognized.
Granulation: Almost good; Granulation tissue formation is weak.
  Good; Granulation tissue is recognized.
  Excellent; Granulation tissue is notably recognized.

For comparison, the results of the control are shown together in Table 4. Simonkolleite of the invention not only exhibits the higher level of reepithelization than that in the control but also leads the regenerated tissue to the equivalent level to healthy skin tissue, particularly in terms of appearance of collagen; an excellent effect of simonkolleite is explicit.

Thus, in this invention, an inorganic material that is the therapeutic agent of the invention is used with an organic material that is a commercial wound covering material, whereby the organic and inorganic materials are hybridized, which produces a great synergy and greatly improves a wound healing ability.

(Evaluation of Test Results)

In view of the respective test results above, followings can be recognized. In healing of wounds, since inflammatory reaction occurs at a pH of 8 or higher, a pH range from neutral to 8 is suitable for a wound healing agent. In view of the pH after the dissolution test with respect to the pH at synthesis (FIGS. 7 and 8), the only pH at synthesis that exceeds the optimum pH is 7.5, and the amount of dissolved $Zn^{2+}$ ions having an important role in the wound healing process is small at this pH value. The above result suggests that, when the pH at synthesis is 7.5, $Zn^{2+}$ ions do not bond to active sites of MMPs, and destruction of the extracellular matrix do not occur, so that migration of cells is not promoted in the wound healing process, whereby wound healing is not promoted. When the pH at synthesis is not around 7.5, the pH falls within the optimum pH range, and dissolution of $Zn^{2+}$ ions is large, so that wound healing is considerably promoted. As shown in Table 4, the evaluation of wound healing in rats satisfies the foregoing discussion. Particularly, it has been revealed through experiments that when the pH at synthesis is 7 at which dissolution of zinc ions is high and which is within the optimum pH range, the wound healing is remarkable. When the pH at synthesis is around 7.5, a specific dissolution behavior is seen, supposedly because it is a transition period between a stage up to the pH of 7 where the recovery rate of simonkolleite in the form of single phase begins to simply increase and a stage of the pH of 8 or higher where a hydroxide phase, e.g., $Zn(OH)_2$, other than simonkolleite becomes dominant. However, the detailed reason therefor has not been clarified at present.

INDUSTRIAL APPLICABILITY

The therapeutic agent of the invention is effective at treating skin wounds or skin roughness extending from the epidermis to the dermis.

Thus, it has a treatment effect on not only severe wounds or skin roughness but also various large and small wounds and skin roughness, and can be widely used as a vulnerary.

The invention claimed is:
1. A therapeutic agent for a skin wound or skin roughness comprising:
  simonkolleite-containing zinc chloride hydroxide hydrate, obtained in a process wherein pH is maintained by a pH controller,
    wherein, after a dissolution test by a stirring method, the simonkolleite-containing zinc chloride hydroxide hydrate has an amount of dissolved $Zn^{2+}$ ions per surface area of 0.25 to 100 $\mu g/m^2$ and a pH of not less than 7.0 but less than 8.3,
    where the dissolution test is conducted with the simonkolleite-containing zinc chloride hydroxide hydrate having a BET specific surface area of 10 to 150 $m^2/g$, a mass ratio between the simonkolleite-containing zinc chloride hydroxide hydrate and saline being 1:50, and stirring being carried out at 500 rpm at 37° C. for 3 hours by means of a rotor.

2. The therapeutic agent for a skin wound or skin roughness according to claim 1, wherein in a pattern of XRD diffraction peaks of the simonkolleite-containing zinc chloride hydroxide hydrate, a structure $Zn_5Cl_2(OH)_8 \cdot nH_2O$ is dominant, with n being 0 to 6, where an a axis is 6.3 to 6.345, and a c axis is 23.4 to 23.7.

3. The therapeutic agent for a skin wound or skin roughness according to claim 1, wherein the simonkolleite-containing zinc chloride hydroxide hydrate is expressed by Formula (1):

$$Zn_{4-6}Cl_{1-3}(OH)_{7-8} \cdot nH_2O \qquad (1)$$

with n being 0 to 6,
and a molar ratio between Zn and Cl is Zn/Cl=2.0 to 4.0.

4. The therapeutic agent for a skin wound or skin roughness according to claim 1, wherein, when the therapeutic agent is dissolved in saline for use with a ratio between the therapeutic agent and saline being 0.1 g/L to 100 g/L, the therapeutic agent being expressed by the Formula (1), and n =0 (anhydrous), a zinc concentration is 45 mass% to 75 mass% in terms of zinc metal with respect to the total amount of the therapeutic agent and a zinc concentration of the therapeutic agent in the saline is 0.045 g/L to 75 g/L.

5. The therapeutic agent for a skin wound or skin roughness according to claim 1, wherein the skin wound or skin roughness is a skin wound or skin roughness extending from epidermis to dermis.

6. The therapeutic agent for a skin wound or skin roughness according to claim 1, further comprising a pharmaceutically acceptable carrier.

7. A medical device for treating a skin wound or skin roughness, comprising: the therapeutic agent for a skin wound or skin roughness according to claim 1 that is applied to a skin wound or skin roughness; and a wound covering material that retains the skin wound or the skin roughness in a closed environment.

8. The medical device for treating a skin wound or skin roughness according to claim 7, wherein the wound covering material is at least one selected from the group consisting of a polyurethane film dressing, a hydrocolloid dressing, a polyurethane foam dressing, an alginate covering material, a hydrogel dressing, a hydropolymer, a cellulose film and a silk film.

9. The medical device for treating a skin wound or skin roughness according to claim 7, wherein the therapeutic agent for a skin wound or skin roughness is applied, contained or attached on or in the wound covering material.

10. A medical set for treating a skin wound or skin roughness, comprising the therapeutic agent for a skin wound or skin roughness according to claim 1 and a wound covering material in combination.

11. An additive for use to add a therapeutic agent for a skin wound or skin roughness as an effective ingredient except the therapeutic agent for a skin wound or skin roughness according to claim 1, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method,
where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

12. An additive for use to add a cosmetic as an effective ingredient, for improving a skin wound or skin roughness to promote beauty effect of the cosmetic, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method,
where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

13. The therapeutic agent for a skin wound or skin roughness according to claim 2, wherein, when the therapeutic agent is dissolved in saline for use with a ratio between the therapeutic agent and saline being 0.1 g/L to 100 g/L, the therapeutic agent being expressed by the Formula (1), and n =0 (anhydrous), a zinc concentration is 45 mass% to 75 mass% in terms of zinc metal with respect to the total amount of the therapeutic agent and a zinc concentration of the therapeutic agent in the saline is 0.045 g/L to 75 g/L.

14. An additive for use to add a therapeutic agent for a skin wound or skin roughness as an effective ingredient except the therapeutic agent for a skin wound or skin roughness according to claim 2, comprising, simonkolleite-containing zinc chloride hydroxide hydrate, obtained in a process wherein pH is maintained by a pH controller, having an amount of dissolved $Zn^{2+}$ ions per surface area of 0.25 to 100μg/m² and a pH of not less than 7.0 but less than 8.3 after a dissolution test by a stirring method,
where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

15. An additive for use to add a therapeutic agent for a skin wound or skin roughness as an effective ingredient except the therapeutic agent for a skin wound or skin roughness according to claim 3, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method,
where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

16. An additive for use to add a therapeutic agent for a skin wound or skin roughness as an effective ingredient except the therapeutic agent for a skin wound or skin roughness according to claim 4, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method, where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

17. An additive for use to add a therapeutic agent for a skin wound or skin roughness as an effective ingredient except the therapeutic agent for a skin wound or skin roughness according to claim 5, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method, where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

18. An additive for use to add a therapeutic agent for a skin wound or skin roughness as an effective ingredient except the therapeutic agent for a skin wound or skin roughness according to claim 6, comprising, simonkolleite-containing zinc chloride hydroxide hydrate, obtained in a process wherein pH is maintained by a pH controller, having an amount of dissolved $Zn^{2+}$ ions per surface area of 0.25 to 100 μg/m² and a pH of not less than 7.0 but less than 8.3 after a dissolution test by a stirring method, where the dissolution test is conducted with the simonkolleite-containing zinc chloride hydroxide hydrate having a BET specific surface area of 10 to 150 m²/g, a mass ratio between the simonkolleite-containing zinc chloride hydroxide hydrate and saline being 1:50, and stirring being carried out at 500 rpm at 37° C. for 3 hours by means of a rotor.

* * * * *